United States Patent
Wilson (10) Patent No.: US 6,599,315 B2
(45) Date of Patent: Jul. 29, 2003

(54) STENT AND STENT DELIVERY ASSEMBLY AND METHOD OF USE

(75) Inventor: W. Stan Wilson, Missoula, MT (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 63 days.

(21) Appl. No.: 09/991,391

(22) Filed: Nov. 20, 2001

(65) Prior Publication Data

US 2002/0035392 A1 Mar. 21, 2002

Related U.S. Application Data

(62) Division of application No. 09/461,946, filed on Dec. 15, 1999, now Pat. No. 6,361,555.

(51) Int. Cl.[7] .......................... A61F 2/06; A61M 29/00
(52) U.S. Cl. ........................ 623/1.11; 606/108
(58) Field of Search .................. 623/1.11, 1.15; 606/108, 194

(56) References Cited

U.S. PATENT DOCUMENTS

| 2,845,959 A | 8/1958 | Sidebotham |
| 2,978,787 A | 4/1961 | Liebig |
| 2,990,605 A | 7/1961 | Demsyk |
| 3,029,819 A | 4/1962 | Starks |
| 3,096,560 A | 7/1963 | Liebig |
| 3,142,067 A | 7/1964 | Liebig |
| 3,657,744 A | 4/1972 | Ersek |
| 3,908,662 A | 9/1975 | Razgulov et al. |
| 3,945,052 A | 3/1976 | Liebig |
| 4,041,931 A | 8/1977 | Elliott et al. |
| 4,047,252 A | 9/1977 | Liebig et al. |
| 4,061,134 A | 12/1977 | Samuels et al. |
| 4,108,161 A | 8/1978 | Samuels et al. |
| 4,140,126 A | 2/1979 | Choudhury |
| 4,193,137 A | 3/1980 | Heck |
| 4,202,349 A | 5/1980 | Jones |
| 4,214,587 A | 7/1980 | Sakura, Jr. |

(List continued on next page.)

FOREIGN PATENT DOCUMENTS

| EP | 0 461 791 A1 | 12/1991 |
| EP | 0 466 518 A3 | 1/1992 |

(List continued on next page.)

OTHER PUBLICATIONS

Lawrence, David D., Jr., M.D., et al., *Percutaneous Endovascular Graft: Experimental Evaluation*, Radiology, vol. 163, No. 2, pp. 357–360 (1987).

(List continued on next page.)

*Primary Examiner*—David H. Willse
*Assistant Examiner*—Suzette J. Jackson
(74) *Attorney, Agent, or Firm*—Fulwider Patton Lee & Utecht, LLP (57) ABSTRACT

A stent delivery catheter assembly for delivering and implanting a stent at or near an area of septal perforators includes a torquing member which, in cooperation with a tracking guide wire and a positioning guide wire, facilitates torquing and rotation of the catheter and hence the position of the stent mounted thereon to accurately position and implant the stent at or near the area of septal perforators. The stent of the present invention has an elongated side aperture which is designed to be implanted next to the area of septal perforators to prevent covering of the orifices of the septal perforators.

6 Claims, 8 Drawing Sheets

U.S. PATENT DOCUMENTS

| | | | |
|---|---|---|---|
| 4,517,687 | A | 5/1985 | Liebig et al. |
| 4,560,374 | A | 12/1985 | Hammerslag |
| 4,562,596 | A | 1/1986 | Kornberg |
| 4,577,631 | A | 3/1986 | Kreamer |
| 4,617,932 | A | 10/1986 | Kornberg |
| 4,652,263 | A | 3/1987 | Herweck et al. |
| 4,693,249 | A | 9/1987 | Schenck et al. |
| 4,728,328 | A | 3/1988 | Hughes et al. |
| 4,732,152 | A | 3/1988 | Wallsten et al. |
| 4,739,762 | A | 4/1988 | Palmaz |
| 4,774,949 | A | 10/1988 | Fogarty |
| 4,787,899 | A | 11/1988 | Lazarus |
| 4,793,348 | A | 12/1988 | Palmaz |
| 4,795,458 | A | 1/1989 | Regan |
| 4,795,465 | A | 1/1989 | Marten |
| 4,817,624 | A | 4/1989 | Newbower |
| 4,830,003 | A | 5/1989 | Wolff et al. |
| 4,872,874 | A | 10/1989 | Taheri |
| 4,878,906 | A | 11/1989 | Lindemann et al. |
| 4,892,539 | A | 1/1990 | Koch |
| 4,969,890 | A | 11/1990 | Sugita et al. |
| 4,969,896 | A | 11/1990 | Shors |
| 4,994,071 | A | 2/1991 | MacGregor |
| 5,026,377 | A | 6/1991 | Burton et al. |
| 5,047,050 | A | 9/1991 | Arpesani |
| 5,104,399 | A | 4/1992 | Lazarus |
| 5,108,424 | A | 4/1992 | Hoffman, Jr. et al. |
| 5,127,919 | A | 7/1992 | Ibrahim et al. |
| 5,156,619 | A | 10/1992 | Ehrenfeld |
| 5,178,630 | A | 1/1993 | Schmitt |
| 5,178,634 | A | 1/1993 | Ramos-Martinez |
| 5,197,976 | A | 3/1993 | Herweck et al. |
| 5,197,977 | A | 3/1993 | Hoffman, Jr. et al. |
| 5,304,220 | A | 4/1994 | Maginot |
| 5,316,023 | A | 5/1994 | Palmaz et al. |
| 5,360,443 | A | 11/1994 | Barone et al. |
| 5,413,560 | A | 5/1995 | Solar |
| 5,443,497 | A | 8/1995 | Venbrux |
| 5,443,498 | A | 8/1995 | Fontaine |
| 5,456,712 | A | 10/1995 | Maginot |
| 5,522,880 | A | 6/1996 | Barone et al. |
| 5,527,355 | A | 6/1996 | Ahn |
| 5,562,724 | A | 10/1996 | Chuter |
| D376,011 | S | 11/1996 | Nunokawa |
| 5,571,170 | A | 11/1996 | Palmaz et al. |
| 5,571,171 | A | 11/1996 | Palmaz et al. |
| 5,571,173 | A | 11/1996 | Parodi |
| 5,575,817 | A | 11/1996 | Martin |
| 5,578,072 | A | 11/1996 | Barone et al. |
| 5,591,228 | A | 1/1997 | Edoga |
| 5,591,229 | A | 1/1997 | Parodi |
| 5,603,721 | A | 2/1997 | Lau et al. |
| 5,609,627 | A | 3/1997 | Goiocoechea et al. |
| 5,613,980 | A | 3/1997 | Chauhan |
| 5,617,878 | A | 4/1997 | Taheri |
| 5,632,763 | A | 5/1997 | Glastra |
| 5,639,278 | A | 6/1997 | Dereume et al. |
| 5,643,340 | A | 7/1997 | Nunokawa |
| 5,669,924 | A | 9/1997 | Shaknovich |
| 5,676,696 | A | 10/1997 | Marcade |
| 5,676,697 | A | 10/1997 | McDonald |
| 5,683,450 | A | 11/1997 | Goicoechea et al. |
| 5,683,452 | A | 11/1997 | Barone et al. |
| 5,683,453 | A | 11/1997 | Palmaz |
| 5,693,084 | A | 12/1997 | Chuter |
| 5,693,086 | A | 12/1997 | Goicoechea et al. |
| 5,693,087 | A | 12/1997 | Parodi |
| 5,693,088 | A | 12/1997 | Lazarus |
| 5,695,517 | A | 12/1997 | Marin et al. |
| 5,709,713 | A | 1/1998 | Evans et al. |
| 5,713,363 | A | 2/1998 | Seward et al. |
| 5,713,917 | A | 2/1998 | Leonhardt et al. |
| 5,718,724 | A | 2/1998 | Goicoechea et al. |
| 5,720,735 | A | 2/1998 | Dorros |
| 5,749,825 | A | 5/1998 | Fischell et al. |
| 5,755,734 | A | 5/1998 | Richter et al. |
| 5,755,735 | A | 5/1998 | Richter et al. |
| 5,755,771 | A | 5/1998 | Penn et al. |
| 5,776,180 | A | 7/1998 | Goicoechea et al. |
| 5,782,906 | A | 7/1998 | Marshall et al. |
| 5,800,508 | A | 9/1998 | Goicoechea et al. |
| 5,800,520 | A | 9/1998 | Fogarty et al. |
| 5,827,320 | A | 10/1998 | Richter et al. |
| 5,893,887 | A | 4/1999 | Jayaraman |
| 5,895,407 | A | 4/1999 | Jayaraman |
| 5,916,234 | A | 6/1999 | Lam |
| 5,916,263 | A | 6/1999 | Goicoechea et al. |
| 5,919,225 | A | 7/1999 | Lau et al. |
| 5,921,995 | A | 7/1999 | Kleshinski |
| 5,938,696 | A | 8/1999 | Goicoechea et al. |
| 5,947,977 | A | 9/1999 | Slepian et al. |
| 5,954,693 | A | 9/1999 | Barry |
| 5,972,017 | A | 10/1999 | Berg et al. |
| 5,976,155 | A | 11/1999 | Foreman et al. |
| 6,030,413 | A | 2/2000 | Lazarus |
| 6,030,414 | A | 2/2000 | Taheri |
| 6,030,415 | A | 2/2000 | Chuter |
| 6,033,434 | A | 3/2000 | Borghi |
| 6,033,435 | A | 3/2000 | Penn et al. |
| 6,039,754 | A | 3/2000 | Caro |
| 6,048,361 | A | 4/2000 | Von Oepen |
| 6,051,020 | A | 4/2000 | Goicoechea et al. |
| 6,096,073 | A | 8/2000 | Webster et al. |
| 6,106,548 | A | 8/2000 | Roubin et al. |
| 6,123,682 | A | 9/2000 | Knudson et al. |
| 6,129,754 | A | 10/2000 | Kanesaka et al. |
| 6,159,237 | A | 12/2000 | Alt et al. |
| 6,165,195 | A | 12/2000 | Wilson et al. |
| 6,183,509 | B1 | 2/2001 | Dibie |
| 6,210,429 | B1 | 4/2001 | Vardi et al. |
| 6,214,041 | B1 | 4/2001 | Tweden et al. |
| 6,221,080 | B1 | 4/2001 | Power |
| 6,221,098 | B1 | 4/2001 | Wilson et al. |
| 6,231,597 | B1 | 5/2001 | Deem et al. |
| 6,238,430 | B1 | 5/2001 | Klumb et al. |
| 6,254,593 | B1 * | 7/2001 | Wilson ..................... 623/1.11 |
| 6,258,116 | B1 | 7/2001 | Hojeibane |
| 6,261,305 | B1 | 7/2001 | Marotta et al. |
| 6,264,682 | B1 * | 7/2001 | Wilson et al. ............. 623/1.11 |
| 6,346,089 | B1 | 2/2002 | Dibie |
| 6,361,555 | B1 * | 3/2002 | Wilson ..................... 623/1.11 |
| 6,371,978 | B1 * | 4/2002 | Wilson ..................... 623/1.11 |
| 6,383,213 | B2 * | 5/2002 | Wilson et al. ............. 623/1.11 |
| 6,387,120 | B2 * | 5/2002 | Wilson et al. ............. 623/1.11 |
| 6,428,567 | B2 * | 8/2002 | Wilson et al. ............. 623/1.11 |
| 6,436,104 | B2 * | 8/2002 | Hojeibane .................. 606/108 |
| 2001/0037137 | A1 | 11/2001 | Vardi et al. |
| 2001/0049548 | A1 | 12/2001 | Vardi et al. |
| 2001/0056297 | A1 | 12/2001 | Hojeibane |

FOREIGN PATENT DOCUMENTS

| | | |
|---|---|---|
| EP | 0 747 020 A2 | 12/1996 |
| EP | 0 804 907 A | 11/1997 |
| FR | 2 737 969 A | 2/1997 |
| SU | 1318235 A1 | 6/1987 |
| SU | 1389778 A2 | 4/1988 |
| SU | 1457921 A1 | 2/1989 |
| SU | 1482714 A2 | 5/1989 |
| WO | WO 95/16406 | 6/1995 |
| WO | WO 95/21592 | 8/1995 |
| WO | WO 96/23455 | 8/1996 |

| | | |
|---|---|---|
| WO | WO 96/24306 | 8/1996 |
| WO | WO 96/24308 | 8/1996 |
| WO | WO 96/34580 | 11/1996 |
| WO | WO 97/07752 | 3/1997 |
| WO | WO 97/15345 | 5/1997 |
| WO | WO 98/19628 | 10/1997 |
| WO | WO 97/41803 | 11/1997 |
| WO | WO 97/45073 | 12/1997 |
| WO | WO 98/36709 | 2/1998 |
| WO | WO 99/34749 | 7/1999 |

OTHER PUBLICATIONS

Yoshioka, Tetsuya, et a., *Self–Expanding Endovascular Graft: An Experimental Study in Dogs, Radiology*, vol. 170, pp. 1033–1037 (1989).

Parodi, J.C., M.D., et al., *Transfemoral Intraluminal Graft Implantation for Abdominal Aortic Aneuyrsms, Annals of Vascular Surgery*, vol. 5, No. 6, pp. 491–499 (1991).

Mirich, David, M.D., *Percutaneously Placed Endovascular Grafts for Aortic Aneurysms: Feasibility Study, Radiology*, vol. 170, No. 3, Part 2, pp. 1033–1037 (1989).

Chuter, Timothy A.M., BM, BS, et al., *Transfemoral Endovascular Aortic Graft Placement, Journal of Vascular Surgery*, pp. 185–196 (Aug., 1993).

Bard XT Catina Bifurcate Stent (Brochure) (Undated).

* cited by examiner

STENT AND STENT DELIVERY ASSEMBLY AND METHOD OF USE

This application is a divisional of U.S. application Ser. No. 09/461,946 filed Dec. 15, 1999, which is now U.S. Pat. No. 6,361,555.

BACKGROUND OF THE INVENTION

The invention relates to stent deployment assemblies for use at a bifurcation and, more particularly, a catheter assembly for implanting one or more stents for treating septal perforation, and a method and apparatus for delivery and implantation.

Stents conventionally repair blood vessels that are diseased and are generally hollow and cylindrical in shape and have terminal ends that are generally perpendicular to their longitudinal axes. In use, the conventional stent is positioned at the diseased area of a vessel and, after placement, the stent provides an unobstructed pathway for blood flow.

Repair of vessels that are diseased at a bifurcation is particularly challenging since the stent must overlay the entire diseased area at the bifurcation, yet not itself compromise blood flow. Therefore, the stent must, without compromising blood flow, overlay the entire circumference of the ostium to a diseased portion and extend to a point within and beyond the diseased portion. Where the stent does not overlay the entire circumference of the ostium to the diseased portion, the stent fails to completely repair the bifurcated vessel. Where the stent overlays the entire circumference of the ostium to the diseased portion, yet extends into the junction comprising the bifurcation, the diseased area is repaired, but blood flow may be compromised in other portions of the bifurcation. Unopposed stent elements may promote lumen compromise during neointimalization and healing, producing restenosis and requiring further procedures. Moreover, by extending into the junction comprising the bifurcation, the stent may block access to portions of the bifurcated vessel that require performance of further interventional procedures. Similar problems are encountered when vessels are diseased at their angled origin from the aorta as in the ostium of a right coronary or a vein graft. In this circumstance, a stent overlying the entire circumference of the ostium extends back into the aorta, creating problems, including those for repeat catheter access to the vessel involved in further interventional procedures.

Conventional stents are designed to repair areas of blood vessels that are removed from bifurcations and, since a conventional stent generally terminates at right angles to its longitudinal axis, the use of conventional stents in the region of a vessel bifurcation may result in blocking blood flow of a side branch or fail to repair the bifurcation to the fullest extent necessary. The conventional stent might be placed so that a portion of the stent extends into the pathway of blood flow to a side branch of the bifurcation or extend so far as to completely cover the path of blood flow in a side branch. The conventional stent might alternatively be placed proximal to, but not entirely overlaying, the circumference of the ostium to the diseased portion. Such a position of the conventional stent results in a bifurcation that is not completely repaired. The only conceivable situation that the conventional stent, having right-angled terminal ends, could be placed where the entire circumference of the ostium is repaired without compromising blood flow, is where the bifurcation is formed of right angles. In such scenarios, extremely precise positioning of the conventional stent is required. This extremely precise positioning of the conventional stent may result with the right-angled terminal ends of the conventional stent overlying the entire circumference of the ostium to the diseased portion without extending into a side branch, thereby completely repairing the right-angled bifurcation.

To circumvent or overcome the problems and limitations associated with conventional stents in the context of repairing diseased bifurcated vessels, a stent that consistently overlays the entire circumference of the ostium to a diseased portion, yet does not extend into the junction comprising the bifurcation, may be employed. Such a stent would have the advantage of completely repairing the vessel at the bifurcation without obstructing blood flow in other portions of the bifurcation. In addition, such a stent would allow access to all portions of the bifurcated vessel should further interventional treatment be necessary. In a situation involving disease in the origin of an angulated aorto-ostial vessel, such a stent would have the advantage of completely repairing the vessel origin without protruding into the aorta or complicating repeat access.

In addition to the problems encountered by using the prior art stents to treat bifurcations, the delivery platform for implanting such stents has presented numerous problems. For example, a conventional stent is implanted in the main vessel so that a portion of the stent is across the side branch, so that stenting of the side branch must occur through the main-vessel stent struts. In this method, commonly referred to in the art as the "monoclonal antibody" approach, the main-vessel stent struts must be spread apart to form an opening to the side-branch vessel and then a catheter with a stent is delivered through the opening. The cell to be spread apart must be randomly and blindly selected by recrossing the deployed stent with a wire. The drawback with this approach is there is no way to determine or guarantee that the main-vessel stent struts are properly oriented with respect to the side branch or that the appropriate cell has been selected by the wire for dilatation. The aperture created often does not provide a clear opening and creates a major distortion in the surrounding stent struts. The drawback with this approach is that there is no way to tell if the main-vessel stent struts have been properly oriented and spread apart to provide a clear opening for stenting the side-branch vessel.

In another prior art method for treating bifurcated vessels, commonly referred to as the "Culotte technique," the side-branch vessel is first stented so that the stent protrudes into the main vessel. A dilatation is then performed in the main vessel to open and stretch the stent struts extending across the lumen from the side-branch vessel. Thereafter, the main-vessel stent is implanted so that its proximal end overlaps with the side-branch vessel. One of the drawbacks of this approach is that the orientation of the stent elements protruding from the side-branch vessel into the main vessel is completely random. Furthermore, the deployed stent must be recrossed with a wire blindly and arbitrarily selecting a particular stent cell. When dilating the main vessel stretching the stent struts is therefore random, leaving the possibility of restricted access, incomplete lumen dilatation, and major stent distortion.

In another prior art device and method of implanting stents, a "T" stern procedure includes implanting a stent in the side-branch ostium of the bifurcation followed by stenting the main vessel across the side-branch ostium. In another prior art procedure, known as "kissing" stents, a stent is implanted in the main vessel with a side-branch stent partially extending into the main vessel creating a double-barreled lumen of the two stents in the main vessel distal to the bifurcation. Another prior art approach includes a so-called "trouser legs and seat" approach, which includes implanting three stents, one stent in the side-branch vessel, a second stent in a distal portion of the main vessel, and a third stent, or a proximal stent, in the main vessel just proximal to the bifurcation.

All of the foregoing stent deployment assemblies suffer from the same problems and limitations. Typically, there is uncovered intimal surface segments on the main vessel and side-branch vessels between the stented segments. An uncovered flap or fold in the intima or plaque will invite a "snowplow" effect, representing a substantial risk for subacute thrombosis, and the increased risk of the development of restenosis. Further, where portions of the stent are left unopposed within the lumen, the risk for subacute thrombosis or the development of restenosis again is increased. The prior art stents and delivery assemblies for treating bifurcations are difficult to use, making successful placement nearly impossible. Further, even where placement has been successful, the side-branch vessel can be "jailed" or covered so that there is impaired access to the stented area for subsequent intervention.

In addition to problems encountered in treating disease involving bifurcations for vessel origins, difficulty is also encountered in treating disease confined to a vessel segment but extending very close to a distal branch point or bifurcation which is not diseased and does not require treatment. In such circumstances, very precise placement of a stent covering the distal segment, but not extending into the ostium of the distal side-branch, may be difficult or impossible.

Problems analogous to the problems described above occur when attempting to treat an area in a vessel surrounding septal perforators. Septal perforators are branch vessels "perforating" into the interventricular septum as branch vessels of either the left anterior descending or posterior descending coronary arteries. Septal perforators are usually multiple and exit in linear fashion from the septal surface of these main vessels as multiple bifurcations. Using a conventional stent in these epicardial vessels often results in plaque shifting and "snowplow" obstruction of multiple septal perforators within the stented segment. This compromises blood flow through the septal perforators. The present invention solves these problems related to treating an area surrounding septal perforators as will be shown.

As used herein, the terms "proximal," "proximally," and "proximal direction" when used with respect to the invention are intended to mean moving away from or out of the patient, and the terms "distal," "distally," and "distal direction" when used with respect to the invention are intended to mean moving toward or into the patient. These definitions will apply with reference to apparatus, such as catheters, guide wires, stents, the like.

SUMMARY OF THE INVENTION

The invention provides for an improved stent design and stent delivery assembly for repairing an area in an artery having septal perforations, without compromising blood flow in other portions of the vessels, thereby allowing access to all portions of the vessels should further interventional treatment be necessary. The stent delivery assembly of the invention has the novel feature of containing, in addition to a tracking guide wire, a positioning guide wire and torquing member that affect rotation and precise positioning of the assembly for deployment of the stent.

In one aspect of the invention, there is provided a longitudinally flexible stent for implanting in a body lumen and expandable from a contracted condition to an expanded condition. The stent includes a cylindrical member having an elongated side aperture. The stent can be used to treat areas proximate to septal perforators without occluding the septal perforators.

In another aspect of the invention, there is provided a stent delivery catheter assembly that includes an elongated catheter. The catheter has an inflation lumen, a tracking guide wire lumen, and a positioning guide wire lumen. An expandable member is positioned at a distal end of the catheter and is in fluid communication with the inflation lumen. A stent is mounted on the expandable member, the stent being longitudinally flexible and for implanting in a body lumen and expandable from a contracted condition to an expanded condition. The stent includes an elongated side aperture such that the stent can be used to treat areas proximate septal perforators without occluding the septal perforators. A torquing member is attached to the tracking guide wire lumen and positioning guide wire lumen so that as the catheter is positioned in a body lumen, the torquing member assists in properly orienting the stent in the lumen.

In another aspect, there is provided a method of stenting a vessel having septal perforation. The method includes the steps of providing a tracking guide wire and tracking guide wire lumen; providing a positioning guide wire and positioning guide wire lumen; providing a torquing member; torquing the positioning guide wire relative to the tracking guide wire with the assistance of the torquing member; and rotating a stent into a desired position within the vessel.

Other features and advantages of the present invention will become apparent from the following detailed description, taken in conjunction with the accompanying drawings, which illustrate, by way of example, the principles of the invention.

DETAILED DESCRIPTION OF THE PREFERRED EMBODIMENTS

As shown in the exemplary drawings wherein like reference numerals indicate like or corresponding elements among the figures, the present invention includes an assembly and method for treating septal perforators.

Figure 1:
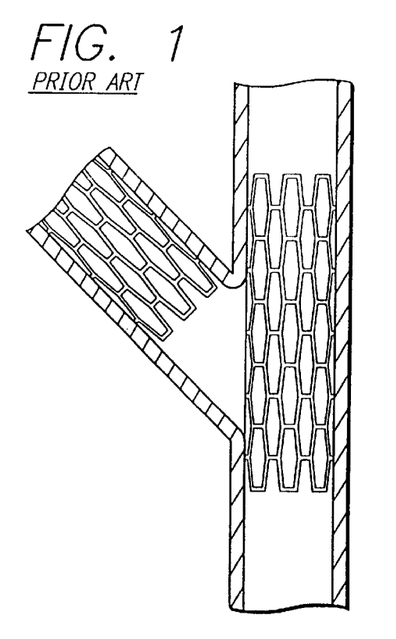
FIG. 1 is an elevational view of a bifurcation in which a prior art "T" stent is in a side-branch ostium followed by the stenting of the main vessel across the branch ostium.

Prior art attempts at implanting intravascular stents in a bifurcation have proved less than satisfactory. For example, FIGS. 1–4 depict prior art devices which include multiple stents being implanted in both the main vessel and a side-branch vessel. In FIG. 1, a prior art "T" stent is implanted such that a first stent is implanted in the side branch near the ostium of the bifurcation, and a second stent is implanted in the main vessel, across the side-branch ostium. With this approach, portions of the side-branch vessel are left uncovered, and blood flow to the side-branch vessel must necessarily pass through the main-vessel stent, causing possible obstructions or thrombosis.

Figure 2:
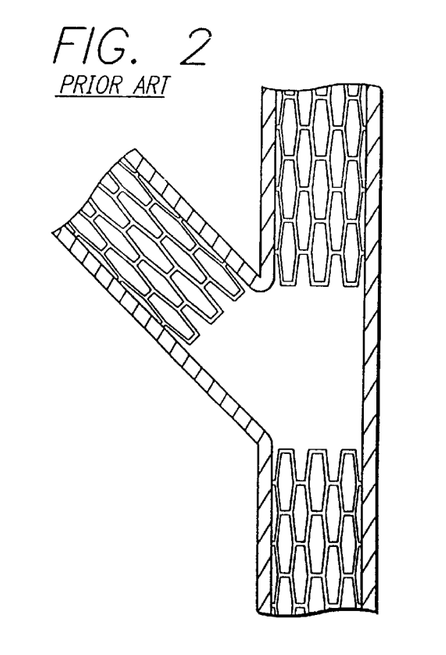
FIG. 2 is an elevational view of a bifurcation in which "touching" prior art stents are depicted in which one stent is implanted in the side branch, a second stent implanted in a proximal portion of the main vessel next to the branch stent, with interrupted placement of a third stent implanted more distally in the main vessel.
Figure 3:
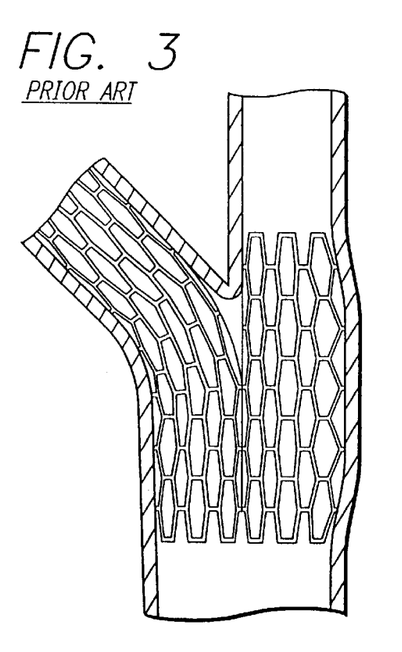
FIG. 3 is an elevational view of a bifurcation depicting "kissing" stents where a portion of one stent is implanted in both the side-branch and the main vessel and adjacent to a second stent implanted in the main vessel creating a double-barreled lumen in the main vessel proximal to the bifurcation.
Figure 4:
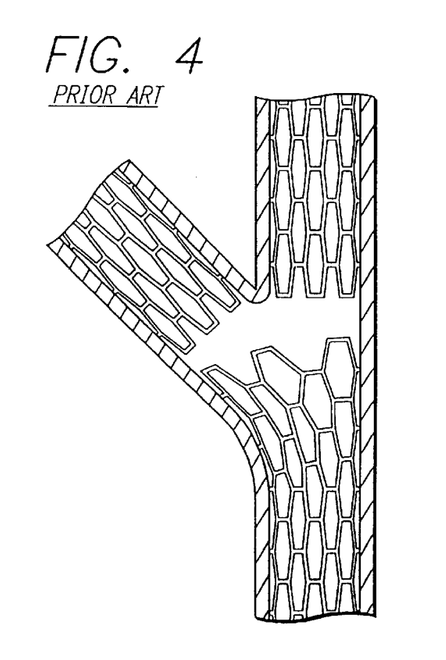
FIG. 4 is an elevational view of a prior art "trouser legs and seat" stenting approach depicting one stent implanted in the side-branch vessel, a second stent implanted in a proximal portion of the main vessel, and a close deployment of a third stent distal to the bifurcation leaving a small gap between the three stents of an uncovered lumenal area.

Referring to FIG. 2, three prior art stents are required to stent the bifurcation. In FIG. 3, the prior art method includes implanting two stents side by side, such that one stent extends into the side-branch vessel and the main vessel, and the second stent is implanted in the main vessel. This results in a double-barreled lumen which can present problems such as thrombosis, and turbulence in blood flow. Referring to the FIG. 4 prior art device, a first stent is implanted in the side-branch vessel, a second stent is implanted in a proximal portion of the main vessel, and a third stent is implanted distal to the bifurcation, thereby leaving a small gap between the stents and an uncovered lumenal area.

Figure 5A:
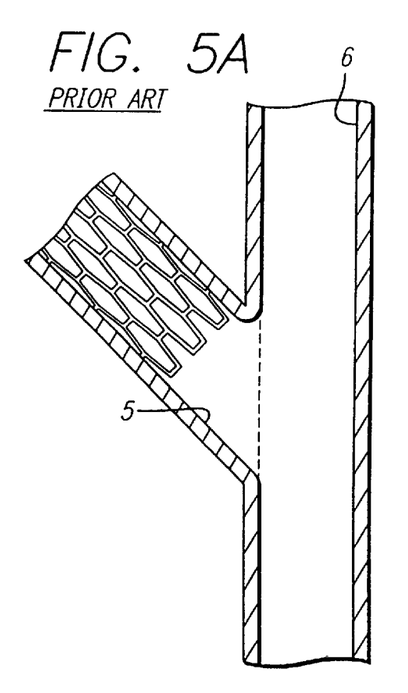
FIG. 5A is an elevational view of a bifurcation in which a prior art stent is implanted in the side-branch vessel.
Figure 5B:
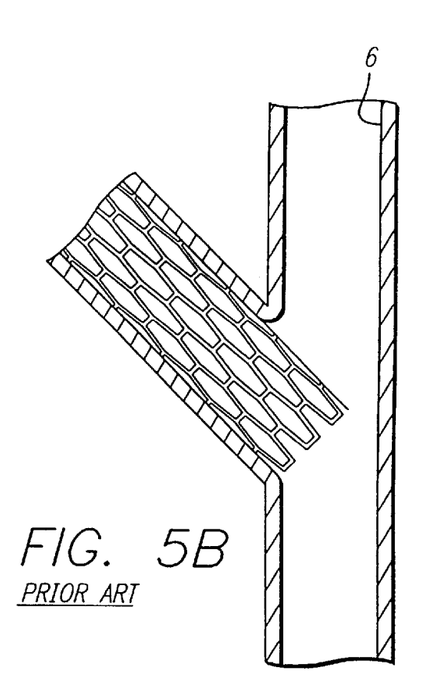
FIG. 5B is an elevational view of a bifurcation in which a prior art stent is implanted in the side-branch vessel, with the proximal end of the stent extending into the main vessel.

Referring to FIGS. 5A and 5B, a prior art stent is configured for deployment in side-branch vessel 5. In treating side-branch vessel 5, if a prior art stent is used, a condition as depicted will occur. That is, a stent deployed in side-branch vessel 5 will leave a portion of the side-branch vessel exposed, or as depicted in 5B, a portion of the stent will extend into main vessel 6.

Figure 6:
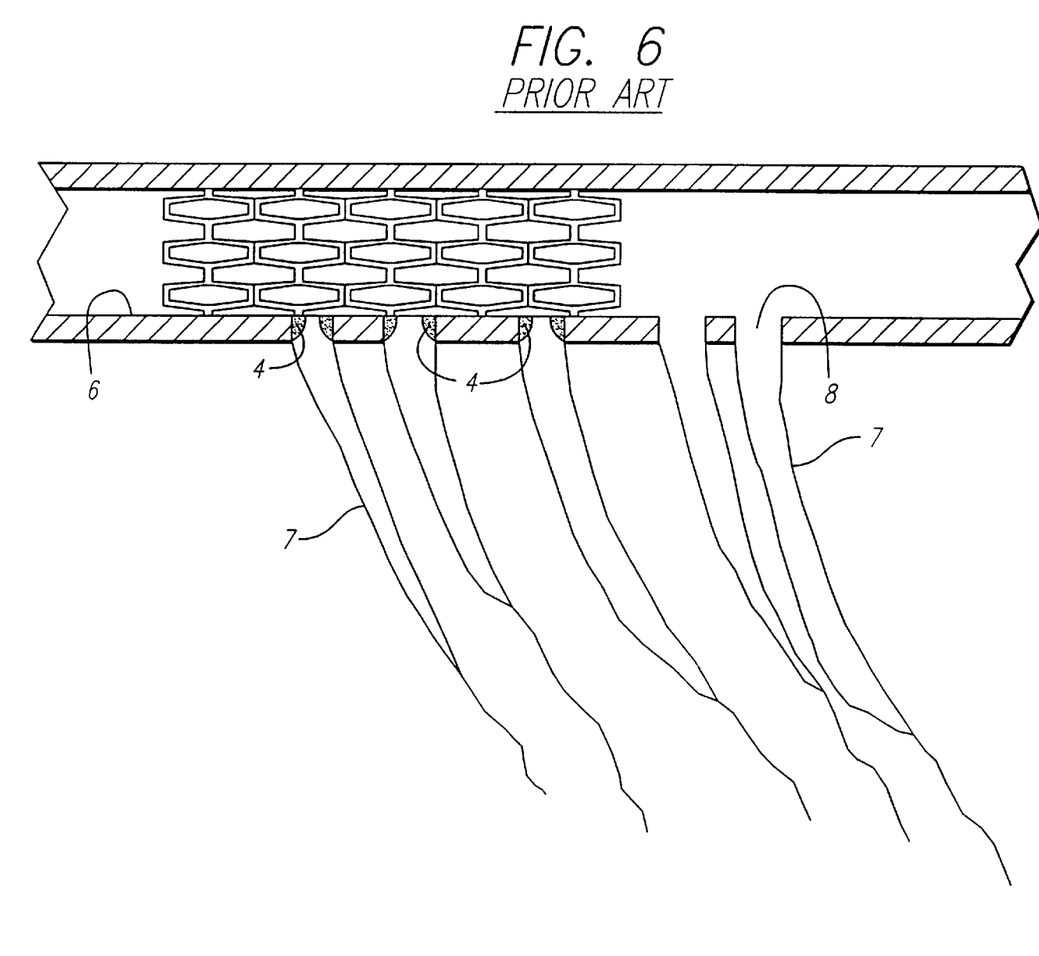
FIG. 6 is an elevational view of an area of a vessel having septal perforators, in which a prior art stent is implanted in the vessel with the stent occluding some of the septal perforators.

Turning to FIG. 6, as mentioned above, similar problems occur when using conventional methods to treat an area in vessel 6 proximate to septal perforators 7. A segment of left anterior descending (or posterior descending) often contains ostia of a sequence of several septal perforators arranged in a linear configuration. Deployment of a conventional stent in this commonly diseased location frequently results in snowplow compromise of the origins, or orifices 8, of these septal perforators. Additionally, a conventional stent can jail orifices 8 leading from main vessel branch 6 to the septal perforators. Furthermore, disease can be snowplowed into the orifices and healthy portions of the vessels. Thus, snowplow obstructions 4 are created in orifices 8, compromising blood flow. While a side aperture stent could be selected to prevent snowplowing in a single septal, it may be more optimal to utilize another stent of a specific design. The present invention solves the problems associated with treating septal perforation.

Figure 7A:
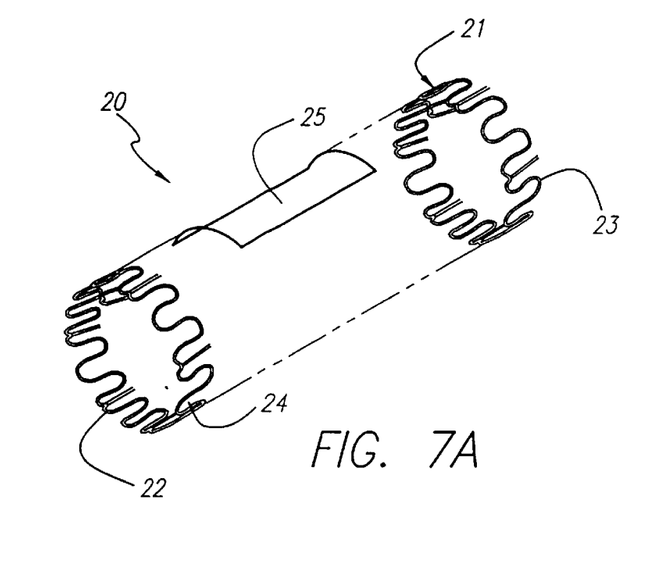
FIG. 7A is a perspective view of a stent of the present invention depicting the elongated side aperture.
Figure 7B:
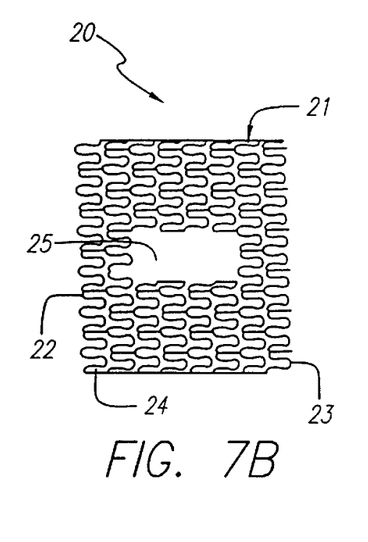
FIG. 7B is a plan view of the stent of FIG. 7A.
Figure 8:
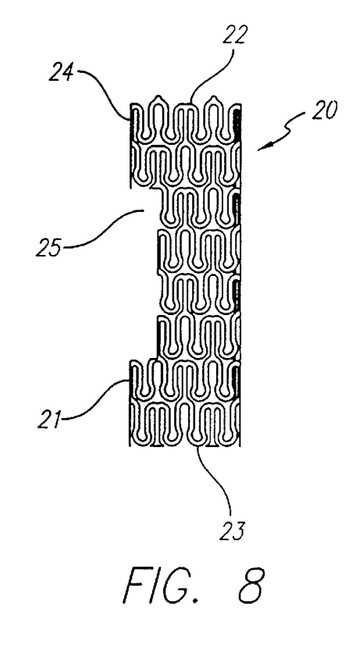
FIG. 8 is an elevational view of the stent of FIG. 7 depicting the elongated side aperture.

In keeping with the invention, as depicted in FIGS. 7A–8, "septal saving" stent 20 is configured for deployment in main vessel 6. Main vessel stent 20 includes cylindrical member 21 having distal end 22 and proximal end 23. Main vessel stent 20 includes outer wall surface 24 which extends between distal end 22 and proximal end 23 and incorporates elongated side aperture 25 on outer wall surface 24. Aperture 25 is configured so that, upon expansion, it is wide enough to cover orifices 8 and long enough to accommodate a desired number of septal perforators. In one embodiment, the elongated side aperture can encompass about 60 degrees of the 360 degrees radius, in which only very limited stent elements, if any, are present to permit radial continuity. However, it is contemplated that greater or lesser ranges of radius can be encompassed. When main vessel stent 20 is implanted and expanded into contact with main vessel 6, aperture 25 is aligned with orifices 8, thereby providing an unrestricted blood flow path from the main vessel through the septal perforators.

Stent 20 can be formed from any of a number of materials including, but not limited to, stainless steel alloys, nickel-titanium alloys (the NiTi can be either shape memory or pseudoelastic), tantalum, tungsten, or any number of polymer materials. Such materials of manufacture are known in the art. Further, the stent can have virtually any pattern known to prior art stents. In one configuration, the stent is formed from a stainless steel material and has a plurality of cylindrical elements connected by connecting members, wherein the cylindrical elements have an undulating or serpentine pattern. Such a stent is disclosed in U.S. Pat. No. 5,514,154 and is manufactured and sold by Advanced Cardiovascular Systems, Inc., Santa Clara, Calif. The stent is sold under the trade name MultiLink® Stent. Such stents can be modified to include the novel features of stent 20.

Stent 20 preferably is a balloon-expandable stent that is mounted on a balloon portion of a catheter and crimped tightly onto the balloon to provide a low profile delivery diameter. After the catheter is positioned so that the stent and the balloon portion of the catheter are positioned in the main vessel, the balloon is expanded, thereby expanding the stent into contact with the vessel. Thereafter, the balloon is deflated and the balloon and catheter are withdrawn from the vessel, leaving the stent implanted. The stent 20 could be made to be either balloon expandable or self-expanding.

Figure 9:
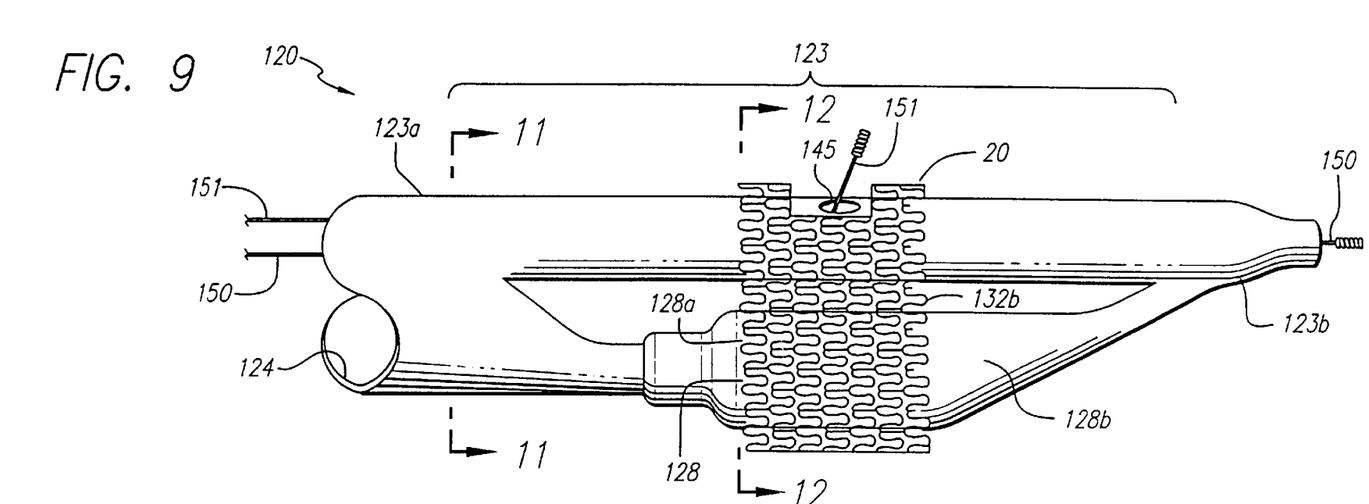
FIG. 9 is an elevational view of the catheter distal section depicting the two guide wire delivery system.
Figure 10:
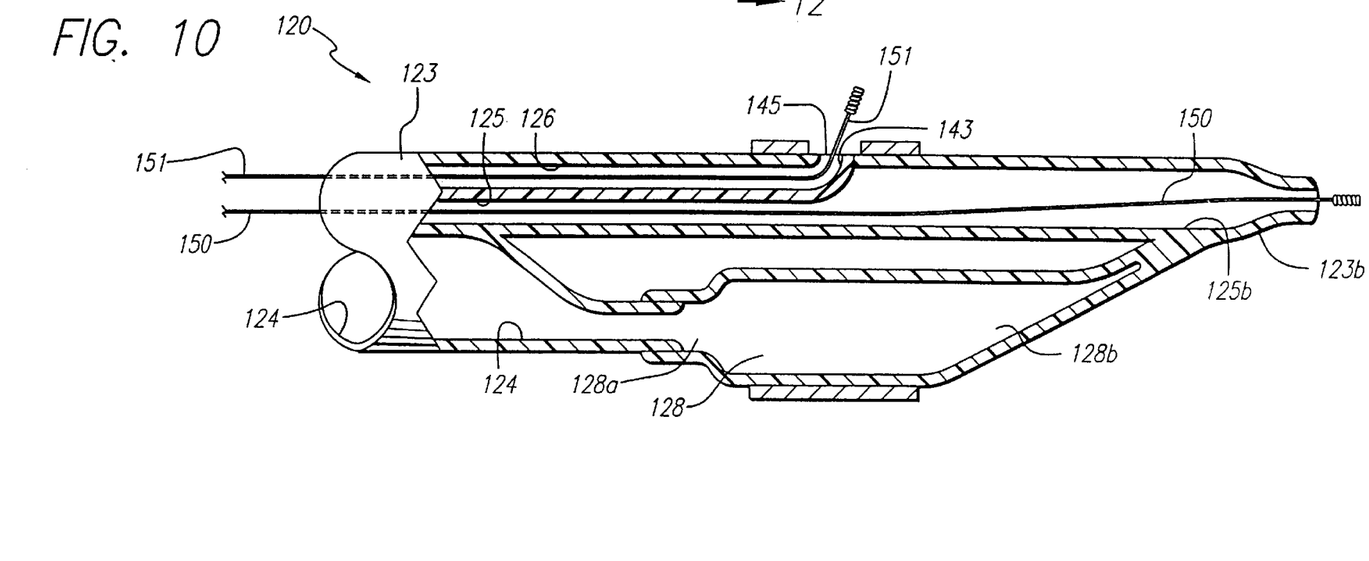
FIG. 10 is a longitudinal cross-sectional view of the catheter distal section of FIG. 9 depicting aspects of the invention.
Figure 11:
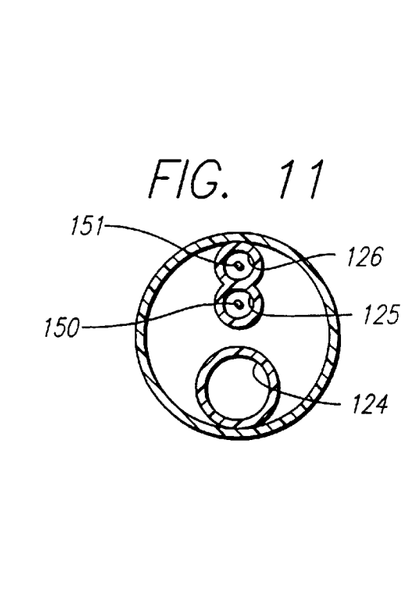
FIG. 11 is a transverse cross-sectional view of the catheter depicting the guide wire lumens and the inflation lumen.
Figure 12:
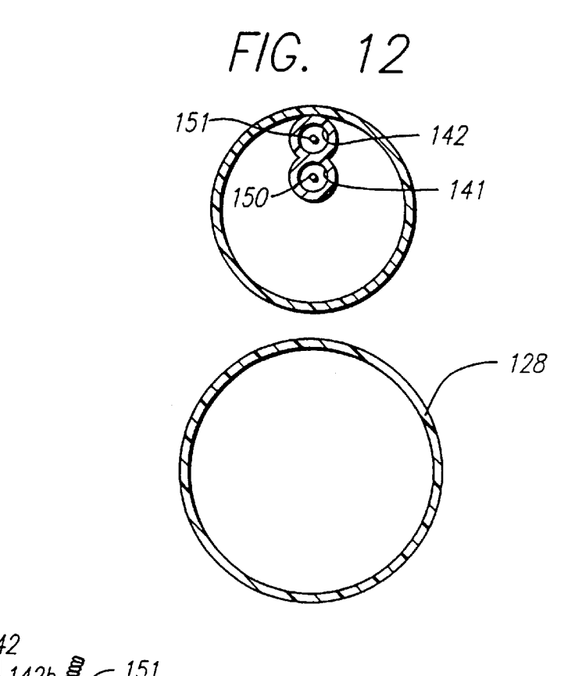
FIG. 12 is a transverse cross-sectional view of the catheter distal section depicting the torquing member and expandable member.
Figure 13:
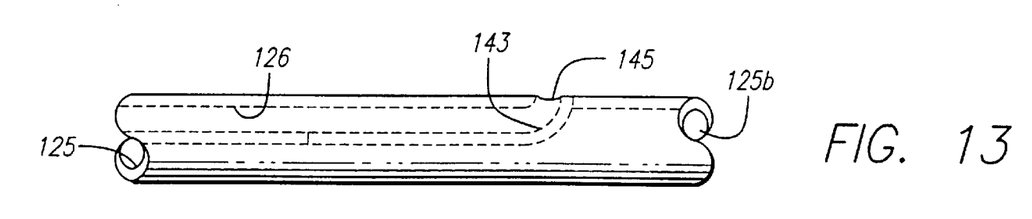
FIG. 13 is a partial elevational view depicting the torquing member in phantom lines.
Figure 14:
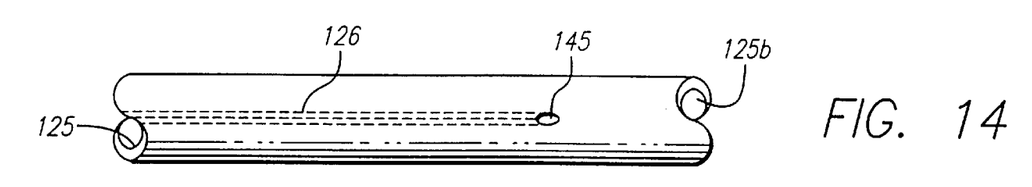
FIG. 14 is a partial elevational view depicting the exit port for the positioning guide wire.

In keeping with the invention, as shown in FIGS. 9–17, a two guide wire delivery catheter assembly 120 is configured to provide maximum torque so that the catheter can be properly positioned in a bifurcated vessel to deliver and implant stent 20. Referring now to FIGS. 9 and 10, elongated catheter 121 is adapted to deliver and implant a stent and it includes proximal end 121a and distal end 121b. The catheter further is defined by distal section 123 which has an inflation lumen 124, a tracking guide wire lumen 125 and a positioning guide wire lumen 126 extending therethrough. An expandable member 128 is positioned at distal section 123 and is in fluid communication with inflation lumen 124. It is contemplated that the tracking guide wire lumen and positioning guide wire lumen could extend along an outer surface of the expandable member. The expandable member preferably extends from proximal end 128a to distal end 128b, however it is preferred that the inflation lumen not run all the way through the expandable member so that the expandable member is lumenless. A lumenless expandable member provides for a smaller profile.

The lumenless expandable member 128 is positioned at a distal end of the catheter 121 and is in fluid communication with the inflation lumen 124. The expandable member distal end 128b is attached to the outer surface of catheter tracking wire lumen distal end 125b. The expandable member is generally a balloon similar to that used in angioplasty procedures. The expandable member is typically non-distensible, having a first compressed diameter for delivery through a vascular system and a second expanded diameter for implanting a stent.

Figure 17:
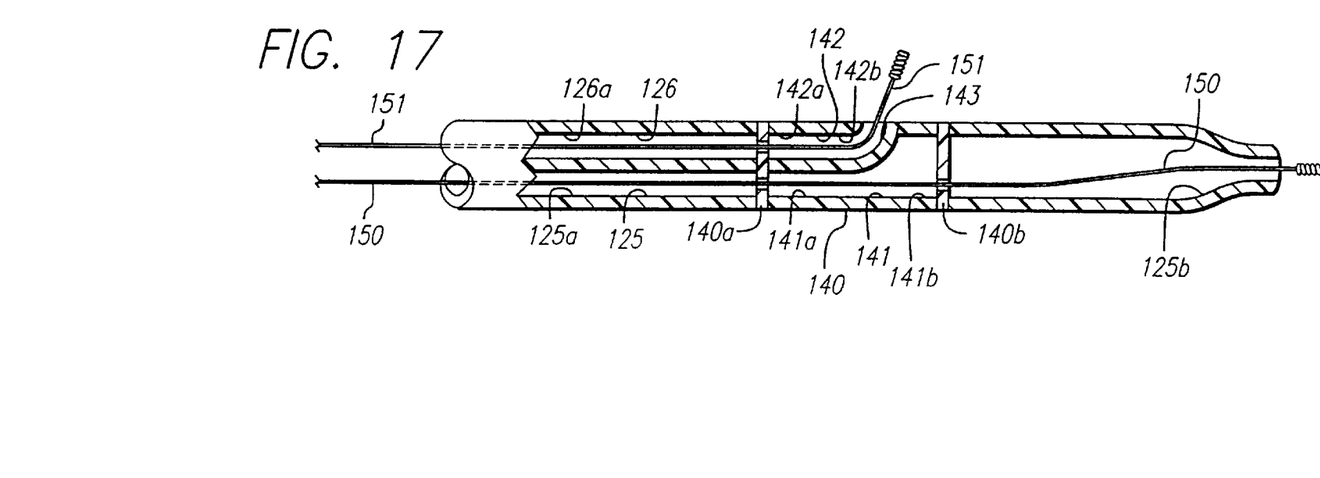
FIG. 17 is a longitudinal cross-sectional view of the catheter distal section and the torquing member.

The present invention provides for a torquing member to assist in torquing the catheter to optimally position the guide wires and properly orient the stent in the vasculature. A torquing member 140, as shown in FIG. 17, is attached to and aligned with tracking wire lumen 125 and positioning guide wire lumen 126. The torquing member is comprised of first port 140a and second port 140b. As depicted in FIG. 17, the torquing member comprises tracking wire lumen 141 and positioning guide wire lumen 142. The torquing member positioning guide wire lumen 142 has a proximal end 142a and a distal end 142b while torquing member tracking guide wire lumen 141 has a proximal end 141a and a distal end 141b. The torquing member tracking guide wire lumen proximal end 141a is aligned with the catheter tracking guide wire lumen 125. The torquing member positioning guide wire lumen proximal end 142a is aligned with the catheter positioning guide wire lumen 126. Thus, there is a substantially continuous guide wire lumen for each of the tracking and positioning guide wire lumens that extend through at least a portion of the catheter, through the torquing member, and the tracking guide wire lumen extends distally of the torquing member. The tracking guide wire lumen 125 slidably receives tracking guide wire 150 and positioning guide wire lumen 126 slidably receives positioning guide wire 151. The tracking guide wire slidably extends through the catheter guide wire tracking lumen and through the torquing member guide wire lumen. The positioning guide wire slidably extends through the catheter positioning guide wire lumen and through the torquing member positioning guide wire lumen where it exits into a vessel. The guide wires 150, 151 preferably are stiff wires each having a diameter of 0.014 inch, but can have different diameters and degrees of stiffness as required for a particular application. A particularly suitable guide wire can include those manufactured and sold under the tradenames Sport® and Ironman®, manufactured by Advanced Cardiovascular Systems, Inc., Santa Clara, Calif.

In keeping with the invention, torquing member 140 further comprises ramp 143 positioned in the positioning guide wire lumen 142. The ramp is positioned in the torquing member and assists the positioning guide wire in advancing through and exiting the catheter. The ramp 143 is sloped and begins a gradual upward slope at the torquing member first port 140a and ends slightly proximal to the torquing member second port 140b. The ramp is distal to the torquing member first port 140a and proximal to the torquing member second port 140b. The ramp ends at opening (or exit port) 145 just proximal to the torquing member second port 140b. The gradual upward slope of the ramp will facilitate the advancement of positioning guide wire 151 so that the guide wire slides up the ramp as it is advanced and it exits the catheter through opening 145 at second port 140b.

Figure 15:
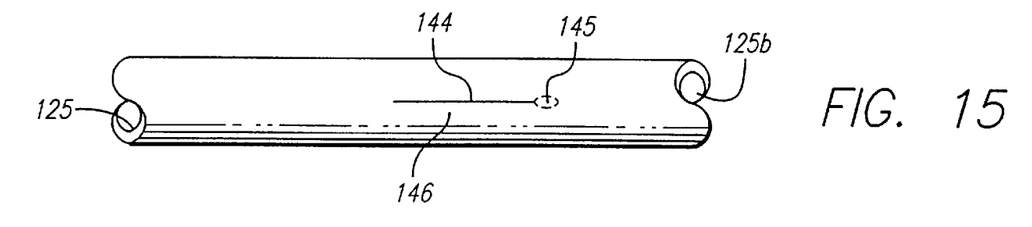
FIG. 15 is a partial elevational view depicting a slit associated with the exit port shown in FIG. 14.
Figure 16:
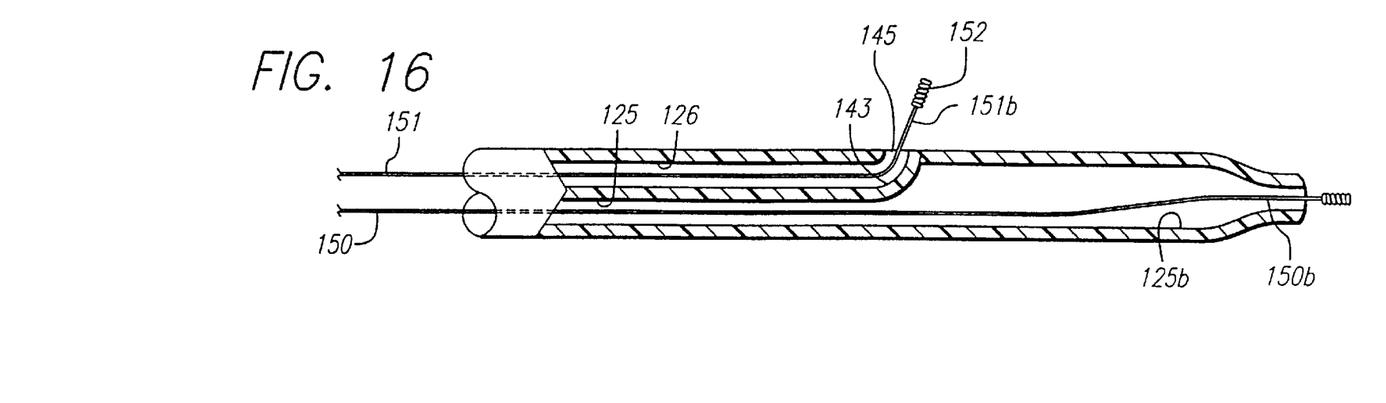
FIG. 16 is a longitudinal cross-sectional view of the catheter distal section and torquing member.

As shown in FIG. 15, the torquing member positioning guide wire lumen 142 preferably has slit 144 in catheter wall 146 located on the side of catheter 121 opposite of opening 145, and is positioned proximal to opening 145. As the positioning guide wire advances through positioning guide wire lumen 126 and slides along ramp 143, it may have a tendency to bend slightly as it encounters frictional resistance along the gradual slope of the ramp. In order to relieve the bending moments in the wire, slit 144 allows the wire to flex into the slit thereby providing a more gradual bend in the positioning guide wire.

The torquing member 140 preferably is formed from a rigid material made from plastic or metal. As shown in FIG. 10, catheter tracking guide wire lumen 125 extends from the torquing member forming a continuous lumen proximal to the torquing member and through it to the catheter distal end.

A stent 20, as shown in FIG. 9, is mounted on the stent delivery catheter assembly 120. The stent has aperture 25 so that the stent does not cover septal perforators in a patient or opening 145 where the positioning guide wire exits. Preferably the stent is mounted on expandable member 128 so that the torquing member is exposed.

The catheter distal section 123 extends from proximal end 123a to distal end 123b. The torquing member 140 can be positioned at any point along the catheter distal section as long as torquing member 140 corresponds with aperture 25 of stent 20.

While the torquing member 140 embodiment has been described in connection with delivery of a stent at septal perforators, its application is broader and can be used to position other devices such as drug delivery means, atherectomy devices, radioactive materials, and the like.

Figure 18:
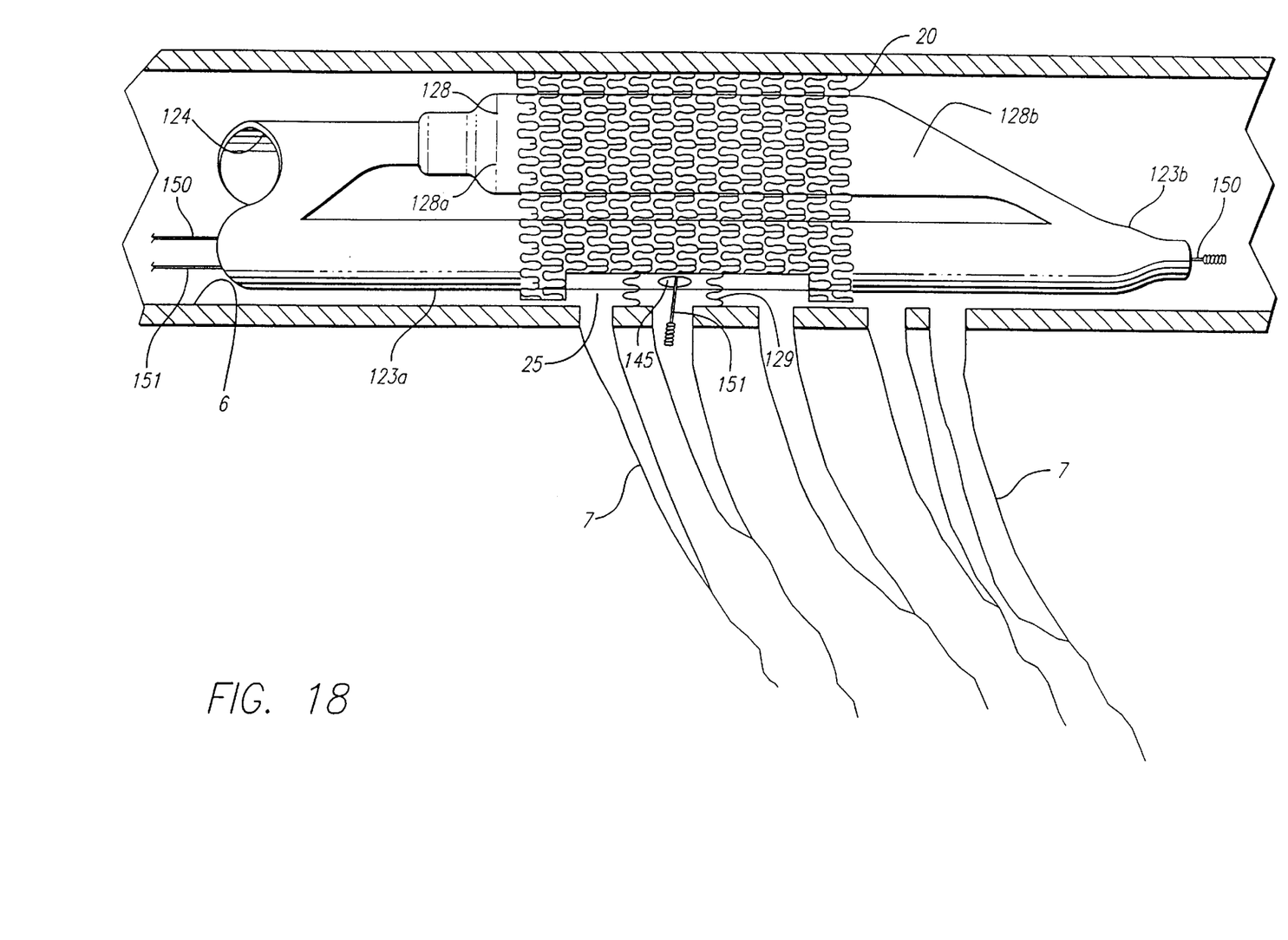
FIG. 18 is an elevational view of the catheter of FIG. 9 at a target site before implantation of a stent.

In further keeping with the invention, as depicted in FIG. 18, stent 20 is mounted on assembly 120 and implanted in vessel 6. The method of achieving stent implantation is as follows.

In keeping with one method of the invention, stent 20 is tightly crimped onto catheter assembly 120 including expandable member 128 for low-profile delivery through the vasculature system. It is particularly critical that aperture 25 of the stent be aligned with opening 145. The distal end of tracking guide wire 150 is advanced into main vessel 6 and distal to the target area, with the proximal end of the tracking guide wire remaining outside the patient. The distal section 123 of the catheter is then advanced, preferably with the use of a guiding catheter (not shown), along the tracking wire until the stent is properly longitudinally positioned at the target area. Up to this point, positioning guide wire 151 resides in positioning guide wire lumen 126 so that the distal end of the positioning wire preferably is near opening 145. This method of delivery prevents the two guide wires from wrapping around each other, the positioning wire being protected by the catheter assembly during delivery.

The distal end of positioning guide wire 151 is then advanced by having the physician push the proximal end from outside the body. The distal end of the integrated positioning guide wire travels through positioning guide wire lumen 126, up ramp 143 whereby the wire is forced to move radially outwardly, and out of opening 145. Preferably, opening 145 is already somewhat aligned with orifice 8 of a septal perforator 7. If not, then some rotation and longitudinal displacement of assembly 120 may be needed in order to advance the positioning guide wire into an orifice of a septal perforator.

After positioning guide wire 151 is advanced into a septal perforator 7, the physician further advances assembly 120 in the distal direction. Due to the assistance of torquing member 140, this action causes the positioning guide wire to push against a wall of the septal perforator, thus creating a torquing force in the positioning guide wire relative to tracking guide wire 150. This torquing force acts to rotate stent 20 such that aperture 25 comes into alignment with orifice 8.

Now expandable member 128 is expanded by known methods, thereby expanding stent 20 into apposition with vessel 6, and thereby implanting the stent in the vessel. As shown in FIG. 18, support struts 129 can be included as part of the stent on each side of opening 145. Thereafter, the expandable member is deflated and catheter assembly 120 is withdrawn from the patient's vasculature. The catheter assembly can be designed so that both tracking guide wire 150 and positioning guide wire 151 can be left in their respective vessels should sequential or simultaneous high pressure balloon inflation be required in vessel 6 in order to complete the stenting procedure. In other words, the wires can be unzipped through slits (not shown) from the catheter thereby allowing the wires to act as a rapid exchange wires.

While the invention herein has been illustrated and described in terms of an apparatus and method for treating septal perforation, it will be apparent to those skilled in the art that the stents and delivery systems herein can be used in the coronary arteries, veins, and other arteries throughout the patient's vascular system. Certain dimensions and materials of manufacture have been described herein, and can be modified without departing from the spirit and scope of the invention.

What is claimed is:

1. A method for treating a vessel with septal perforators, comprising:

providing an elongated catheter having an expandable member positioned thereon, tracking guide wire disposed within a tracking guide wire lumen and a positioning guide wire disposed within a positioning guide wire lumen, said positioning guide wire lumen having a distal opening formed in said catheter adjacent said expandable member;

providing a torquing member attached to both said tracking guide wire lumen and said positioning guide wire lumen;

positioning an expandable stent having a side aperture on said catheter so as envelop said expandable member and such that said distal opening of said positioning guide wire is aligned with a portion of said aperture;

advancing said catheter through a vessel having septal perforators along said tracking guide wire to a position wherein said stent is substantially longitudinally aligned and wherein said positioning guide wire lumen opening is generally radially aligned with said septal perforators;

advancing said positioning guide wire so as to emerge from said distal opening in said positioning guide wire and enter one of said septal perforators;

further advancing said catheter in a distal direction so as to cause said catheter and stent to rotate into substantial alignment with said septal perforators by torque created by the positioning guide wire and tracking guide wire which is transferred to the catheter by said torquing member; and expanding said expandable member to expand said stent.

2. The method of claim 1, wherein said expandable stent has multiple side apertures formed therein.

3. The method of claim 2, wherein each of said apertures is aligned with one of said septal perforators.

4. The method of claim 1, wherein said side aperture is elongated.

5. The method of claim 4, wherein said aperture is aligned with a plurality of said septal perforators.

6. The method of claim 1, wherein said aperture encompasses about 60 degrees of said stent's circumference.

* * * * *